United States Patent [19]

Nösberger

[11] Patent Number: 4,904,805
[45] Date of Patent: Feb. 27, 1990

[54] PROCESS FOR MANUFACTURING A DIKETONE

[75] Inventor: Paul Nösberger, Birsfelden, Switzerland

[73] Assignee: Hoffmann-La Roche Inc., Nutley, N.J.

[21] Appl. No.: 682,123

[22] Filed: Dec. 17, 1984

Related U.S. Application Data

[63] Continuation of Ser. No. 461,043 Jan 26, 1983 abandoned.

[30] Foreign Application Priority Data

Feb. 12, 1982 [CH] Switzerland .............................. 889/82

[51] Int. Cl.$^4$ .............................................. C07D 307/28
[52] U.S. Cl. .................................................... 549/319
[58] Field of Search ...................................... 549/319, 9

[56] References Cited

U.S. PATENT DOCUMENTS

| | | | |
|---|---|---|---|
| 1,614,195 | 1/1927 | Haussler | 560/174 |
| 1,627,091 | 5/1927 | Haussler | 560/174 |
| 3,843,555 | 10/1974 | Erpenbach | 252/470 |
| 4,225,506 | 9/1980 | Schmid | 260/343.6 |

FOREIGN PATENT DOCUMENTS 2403042  8/1974  Fed. Rep. of Germany .

OTHER PUBLICATIONS

Beilsteins Handbuch der Organischen Chemie, 4th edition, Suppl. III/IV, vol. 17(7), p. 5848 (1975).
Champetier, C. R., Acad. Sc. Paris (C) 262 1891–1893 (1966).
Doleschall, G. et al., Tetrahderon 36:1649–1665 (1980).
Kuhn et al., Chem. Ber. 75B, 121–123 (1942), Chem. Abst. 37:2717$^6$ (1943).
S. H. Lipton et al., J. Amer. Chem. Soc. 71, 2364–2367 (1949).
O. Nagase et al., Chem. Pharm. Bull. 17(2), 398–399 (1969).
Derwent (62344B/34 Bo3) abstract of J5 4088-257, 07-13-79.

Primary Examiner—Richard L. Raymond
Assistant Examiner—Ba K. Trinh
Attorney, Agent, or Firm—George M. Gould; Bernard S. Leon; George W. Johnston

[57] ABSTRACT

A process for the manufacture of ketopantolactone of the formula

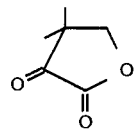

I from pantolactone, which comprises dehydrogenating pantolactone in the presence of a vanadium oxide-containing or molybdenum oxide-containing catalyst with oxygen or an oxygen-containing gas in the gas phase.

13 Claims, No Drawings

PROCESS FOR MANUFACTURING A DIKETONE

This is a continuation of U.S. application Ser. No. 461,043, filed Jan. 26, 1983, now abandoned.

BACKGROUND OF THE INVENTION

1. Field of the Invention

The present invention is concerned with a novel process for producing keptopantolactone(dihydro-4,4-dimethyl-2,3-furandione).

2. Description of the Prior Art

Ketopantolactone is an important starting material for manufacturing optically active pantolactone (dihydro-3-hydroxy-4,4-dimethyl-2(3H)-furanone), which is used in the manufacture of biologically active pantothenic acid.

Several prior art processes for producing ketopantolactone are known. In the prior art, racemic pantolactone was oxidized to ketopantolactone by utilizing lead tetraacetate, N-bromosuccinimide or chromium trioxide (Jones' reagent) as the oxidizing agent. This prior art procedure disadvantageously resulted in relatively low yield of ketopantolactone, and the oxidizing agent was expensive. In the prior aer, this process has been modified by using bromine or alkali or alkaline earth metal hypochlorites in the organic phase.

In another prior art process, dimethylpyruvic acid and formaldehyde were utilized to manufacture ketopantolactone. Disadvantageously this process also suffered from obtaining only relatively low yields and its end product was not entirely pure even after distillation.

SUMMARY OF THE INVENTION

This invention relates to a process for producing ketopantolactone.

In accordance with the invention pantolactone is dehydrogenated to ketopantolactone. The process occurs in the presence of a vanadium oxide- or molybdenum oxide-containing catalyst with oxygen or an oxygen containing gas as the oxidizing agent while the pantolactone is in the gas phase.

The process of the present invention avoids the disadvantages of the prior art by providing high yields of ketopantolactone without using expensive oxidizing reagents.

DETAILED DESCRIPTION OF THE INVENTION

The present invention relates to a process for producing ketopantolactone.

In accordance with the invention, ketopantolactone of the formula

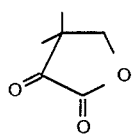

I is manufactured from pantolactone of the formula

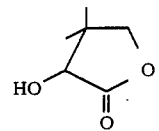

II by dehydrogenating pantolactone of formula II in the presence of a vanadium oxide- or molybdenum oxide-containing catalyst with oxygen or an oxygen-containing gas while the pantolactone is in the gas phase.

The inventive process constitutes an oxidative dehydrogenation of pantolactone and leads in good yield to the desired ketopantolactone. Since this process can be carried out especially utilizing air as the "oxygen-containing gas", the use of expensive oxidation agents is avoided. Moreover, this process is readily usable on a technical scale and also can be carried out especially continuously.

Advantageously, the byproducts of the inventive process mainly are water, carbon dioxide and carbon monoxide, so that, after separating out the water and further low-boiling byproducts, a product of high purity is obtained directly.

Further, the inventive process can be carried out with technical pantolactone (purity about 79–92% by weight). With technical pantolactone a better selectivity and, in addition, a purification effect is achieved, since a part of the impurities is destroyed during the process.

The inventive oxidative dehydrogenation of pantolactone is carried out while the pantolactone is maintained in a gas phase and in the presence of a vanadium- or molybdenum oxide-containing catalyst. For example the catalyst contains vanadium or molybdenum oxide, a vanadate or molybdate of a transition metal or a mixture of such compounds. Preferred among such vanadium and molybdenum compounds are vanadium pentoxide, molybdenum trioxide and the vandates and molybdates of iron, nickel, silver, copper and cobalt. Furthermore these catalysts can, if desired, also contain other metals such as, for example, tin, antimony, bismuth, lead and the like. Examples of preferred catalysts are vanadium pentoxide, mixtures of vanadium pentoxide or iron (III) oxide with molybdenum trioxide, iron-silver molybdate, nickel vanadate, copper vanadate, silver vanadate, iron-silver vanadate or cobalt vanadate. Catalysts which contain vanadium pentoxide and/or molybdenum trioxide are especially preferred.

The catalyst can be present in pure form, can be mixed with an inert carrier material or can be fixed on an inert, formed carrier material. Examples of inert carrier materials are α-aluminium oxide, ceramics, kieselguhr, glass, silicon carbide and the like. Catalysts which are fixed on an inert carrier material are preferred. α-Aluminium oxide and ceramics are preferred carrier materials. The use of vanadium pentoxide or a mixture of vanadium pentoxide and molybdenum trioxide on α-aluminium oxide as the catalyst is quite especially preferred.

The catalysts used in the inventive process are commercially obtainable or can be prepared readily from known compounds by conventional techniques. They have a long lifespan and show no decrease in activity even after several months use. Likewise, the selectivity of the catalysts remains constant. The process in accordance with the invention can therefore advantageously be carried out also in a packed bed reactor.

Oxygen or an oxygen-containing gas is used in accordance with the invention as the oxidation agent. The term "oxygen-containing gas" signifies generally a mixture of oxygen and an inert gas, such as, for example, nitrogen, carbon dioxide, argon and/or steam. The oxygen content of the mixture is not critical. However, in general it amounts to about 1–40 vol-% and preferably about 5–21 vol-%. Especially preferred is the use of air, to which can be added, if desired, nitrogen and/or exhaust gases from the reactor (after separation of ketopantolactone) to control the rate of reaction and to remove reaction heat.

The amount of oxygen or oxygen-containing gas is not critical at the upper end. In order to achieve a conversion which is as complete as possible, at least about 1 mol of oxygen should be added to the reactor per mol of pantolactone. However, the reaction preferably is performed with an excess of oxygen, for example with about 200–2000% (by volume) and preferably with about 300–1000% (by volume) excess.

The inventive oxidative dehydrogenation of pantolactone is strongly exothermic and temperature dependent. At too high a temperature the total oxidation can become the main reaction, which may lead to the reactor becoming uncontrolable. The optimum temperature is dependent on the catalyst used, the oxygen and pantolactone concentration in the educt stream, the purity of the pantolactone, the gas velocity, the form and size of the reactor and the like. In general, the reaction is performed within a temperature range of about 150°–400° C., preferably about 200°–350° C. A temperature range of about 250°–300° C. is especially preferred.

Suitable materials for the reactor vessel are all conventionally used materials which do not affect pantolactone and ketopantolactone under the reaction conditions, such as, for example, stainless steel, glass, ceramics and the like.

In the inventive process, the amount of catalyst is not critical. The optimum amount depends upon the selected catalyst, temperature, form and size of the reactor, amount of educt employed and the like. The optimization is conveniently carried out by charging the catalyst and, if desired, inert carrier material into the reactor (preferably a packed bed reactor) and then by conventional techniques adjusting the residence time of the educt and the temperature so that the conversion to pantolactone is as high as possible, preferably over about 90%.

Afte separating out the water and the low-boiling byproducts by conventional techniques, the process yields the desired ketopantolactone in a purity of about 99%. The separation can be effected, for example, by cooling and, if desired, additional washing of ketopantolactone with water. As mentioned above, the exhaust gases can, if desired, again be added to the reactor. If desired, the product obtained can be purified further, for example by crystallization in toluene or diethyl ether or by rectification.

The invention is further concerned with all novel compounds, mixtures processes and uses as herein described.

The following examples further illustrate the invention. Percentages are expressed by weight, except those for the transformation rates and selectivity which are mole percents. Temperatures are in degrees Celsius. Unless indicated otherwise, the examples were performed as written. Harshaw is a manufacturer of catalysts located at Cleveland, Ohio, USA. Girdler also is a catalyst manufacturer located at Munich, Germany. Rosenthal is a ceramics manufacturer located at Selb, Germany.

EXAMPLE 1

The reactor consists of a thermostatible conventional vessel (95° C.) for pantolactone, which is attached to a dosage pump, an air stream control, an electrically heated evaporation tube (250° C., length 20 cm) and a reaction tube (length 60 cm, diameter 3.5 cm), which is surrounded by an air bath (250° C.) and which is connected at the upper end with the evaporation tube. The tube portions are constructed from stainless steel. The catalyst used is $\alpha$-aluminium oxide coated with 6% vanadium pentoxide and 3% molybdenum trioxide (obtainable from Harshaw under the name V-1002E). The evaporation tube as well as the uppermost and lowermost 10 cm of the reaction tube are filled with ceramic balls. The remaining 40 cm of the reaction tube (reaction zone) are provided at the bottom (20 cm deep) with catalyst, in the middle (10 cm deep) with catalyst and ceramic balls in the ratio 1:1 and at the top (10 cm deep) with catalyst and ceramic balls in the ratio 1:3. 100 l of air and 43 g of pantolactone are now added hourly to the evaporator. The temperature rises at the hottest position in the reaction zone to about 290° C. and at the outflow from the reaction zone to about 250° C. 99.3% of the pantolactone are transformed and ketopantolactone is formed with a selectivity of 86.2%. Water and carbon dioxide are primarily formed as byproducts. After separating the reaction water and traces of low-boiling byproducts on a rotary evaporator at 60° C. and under a water-jet vacuum, there is obtained ketopantolactone with a purity of about 99%. By recrystallization in toluene there is obtained ketopantolactone with a purity of 99.9%; m.p. 67° C., b.p. 248° C.

EXAMPLE 2

$\alpha$-Aluminium oxide coated with 10% vanadium pentoxide (V-0501S from Harshaw) is used as the catalyst in the reactor described in Example 1 and the temperature of the air bath is adjusted to 245° C. 60 l of air and 33 g of pantolactone are subsequently added hourly to the evaporator. 99% of the pantolactone are transformed and ketopantolactone is formed with a selectivity of 85%.

EXAMPLE 3

A mixture of iron (III) oxide and molybdenum trioxide (G-105 from Girdler) is used as the catalyst in the reactor described in Example 1 and the temperature of the air bath is adjusted to 225° C. 60 l of air and 33 g of pantolactone are subsequently added hourly to the evaporator. 96% of the pantolactone are transformed and ketopantolactone is formed with a selectivity of 83%.

EXAMPLE 4

An iron-silver molybdate on ceramic is used as the catalyst in the reactor described in Example 1 and the temperature of the air bath is adjusted to 245° C. 60 l of air and 32 g of pantolactone are subsequently added hourly to the evaporator. 97.8% of the pantolactone are transformed and ketopantolactone is formed with a selectivity of 78.7%.

The catalyst used can be prepared as follows:

A solution of 24.72 g of ammonium heptamolybdate tetrahydrate in 500 ml of water is treated dropwise while stirring well with a solution of 12.12 g of iron (III) nitrate nonahydrate and 5.10 g of siler nitrate in 100 ml of water. The precipitate is filtered off under suction, washed with water and then added together with 300 g of carrier (ceramic balls with a diameter of 6 mm, obtainable from Rosenthal under the name RST F1/Sp) to a wide-necked flask and covered with water. The water is subsequently removed on a rotary evaporator with the slowest possible rotation at 90° C. with the aid of an air stream. The catalyst obtained is finally heated at 450° C. for a further 16 hours.

EXAMPLE 5

Nickel vanadate on ceramic is used as the catalyst in the reactor described in Example 1 and the temperature of the air bath is adjusted to 270° C. 100 l of air and 32 g of pantolactone are subsequently added hourly to the evaporator. 99.2% of the pantolactone are transformed and ketopantolactone is formed with a selectivity of 79.8%.

The catalyst used can be prepared as follows:

A solution of 16.98 g of nickel nitrate in 50 ml of water is added slowly while stirring well to a solution, warmed to 60° C., of 13.66 g of ammonium vanadate in 1000 ml of water, the mixture is then concentrated on a rotary evaporator and cooled. The precipitate obtained is filtered off under suction, washed, fixed to ceramic balls in a manner analogous to that described in Example 4 and the catalyst obtained is heated at 500° C. for 16 hours.

EXAMPLE 6

Copper vanadate on ceramic is used as the catalyst in the reactor described in Example 1 and the temperature of the air bath is adjusted to 250° C. 60 l of air and 32 g of pantolactone are added hourly to the evaporator. 99.0% of the pantolactone are transformed and ketopantolactone is formed with a selectivity of 77.5%.

The catalyst used can be prepared as follows:

A solution of 9.96 g of copper (II) chloride dihydrate in 50 ml of water is added slowly while stirring well to a solution, warmed to 60° C., of 13.66 g of ammonium vanadate in 1000 ml of water. The precipitate obtained is filtered off under suction, washed, fixed to ceramic balls in a manner analogous to that described in Example 4 and the catalyst obtained is heated at 500° C. for 16 hours.

EXAMPLE 7

Silver vanadate on ceramic is used as the catalyst in the reactor described in Example 1 and the temperature of the air bath is adjusted to 250° C. 60 l of air and 27 g of pantolactone are subsequently added hourly to the evaporator. 98.4% of the pantolactone are transformed and ketopantolactone is formed with a selectivity of 84.4%.

The catalyst used can be prepared as follows:

A solution of 15.5 g of silver nitrate in 125 ml of water is added slowly while stirring well to a solution, warmed to 60° C., of 8.78 g of ammonium vanadate in 1000 ml of water. The precipitate obtained is filtered off under suction, washed, fixed to ceramic balls in a manner analogous to that described in Example 4 and the catalyst obtained is heated at 500° C. for 16 hours.

EXAMPLE 8

Technical pantolactone (content 83.5%) is reacted in an analogous manner to that described in Example 1. The temperature of the air bath is adjusted to 270° C. and 60 l of air and 41 g of technical pantolactone are added hourly to the evaporator. 99% of the pantolactone are transformed and ketopantolactone is formed with a selectivity of 92% (based on pantolactone).

I claim:

1. A process for producing ketopantolactone of the formula

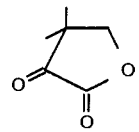

I from pantolactone of the formula

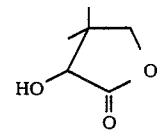

II comprising dehydrogenating pantolactone of formula II in the presence of a vanadium oxide- or molybdenum oxide-containing catalyst with oxygen or an oxygen-containing gas while the pantolactone is in the gas phase.

2. The process of claim 1 wherein the catalyst used contains vanadium pentoxide, molybdenum trioxide, or a vanadate or molybdate of iron, nickel, silver, copper or cobalt.

3. The process of claim 2 wherein the catalyst used contains vanadium pentoxide or molybdenum trioxide.

4. The process of claim 1 wherein the catalyst is fixed on an inert carrier material.

5. The process of claim 4 wherein the inert carrier material is α-aluminium oxide or a ceramic.

6. The process of claim 5, wherein the catalyst is vanadium pentoxide or a mixture of vanadium pentoxide and molybdenum trioxide fixed on α-aluminium oxide.

7. The process of claim 1, wherein the oxygen containing gas is air.

8. The process of claim 7 wherein the oxygen containing gas is air and an inert gas selected from the group consisting of nitrogen and exhaust gases produced during the process.

9. The process of claim 7 wherein the dehydrogenation is carried out with an excess of an oxygen-containing gas.

10. The process of claim 1 wherein the dehydrogenation is carried out at a temperature of about 150° C. to about 400° C.

11. The process of claim 10 wherein the dehydrogenation is carried out at about 200° C. to about 350° C.

12. A process for producing ketopantolactone from pantolactone in a reactor vessel charged with a vanadium oxide- or molybdenum oxide-containing catalyst, the process comprising:

(a) adding oxygen or an oxygen-containing gas to the vessel;

(b) adding pantalactone to the vessel;

(c) adjusting the temperature within the reaction vessel so that the pantolactone is in a vapor phase, thereby forming ketopantolactone.

13. A process for producing ketopantolactone from pantolactone in a reactor vessel charged with vanadium pentoxide or a mixture of vanadium pentoxide and molybdenum trioxide on α-aluminium oxide catalyst, the process comprising:
(a) adding air to the reaction vessel;
(b) adding pantolactone to the reaction vessel;
(c) maintaining the temperature of the process between about 250° C. and about 300° C.,
thereby dehydrogenating the pantolactone to ketopantolactone.

* * * * *